United States Patent [19]

Wang

[11] Patent Number: 4,908,458

[45] Date of Patent: Mar. 13, 1990

[54] KETOHETEROCYCLIC DERIVATIVES

[75] Inventor: Pen C. Wang, Houston, Tex.

[73] Assignee: Shell Oil Company, Houston, Tex.

[21] Appl. No.: 284,873

[22] Filed: Dec. 15, 1988

[51] Int. Cl.$^4$ .................. C07D 403/06; C07D 413/06; C07D 417/06
[52] U.S. Cl. .................................... 548/328; 548/156; 548/219
[58] Field of Search ..................... 548/328, 219, 156

[56] References Cited

U.S. PATENT DOCUMENTS

| | | | |
|---|---|---|---|
| 3,661,849 | 5/1972 | Culbertson | 548/328 |
| 3,673,202 | 6/1972 | Orlando | 548/328 |
| 4,585,575 | 4/1986 | Heiss | 548/219 |

*Primary Examiner*—Robert Gerstl

[57] ABSTRACT

Novel, thermoplastic heterocyclic-substituted 3-oxopentane derivatives, and the method of their production by reaction of an o-phenylene amine compound and the source of a five-carbon keto-containing moiety selected from 4-oxoheptanedioic acid compounds or 1,6-dioxa [4.4] spirodilactones.

12 Claims, No Drawings

KETOHETEROCYCLIC DERIVATIVES

FIELD OF THE INVENTION

This invention relates to production of a novel class of benzoheterocyclic compounds additionally having keto functionality, and to the compounds thereby produced. More particularly, the invention relates to the reaction of an o-phenylene amine compound and a 4-oxoheptanedioic acid compound or a 1,6-dioxa [4.4] spirodilactone, either of which serves as the source of the five-carbon, keto-containing moiety linking together benzoheterocyclic ring systems in the compounds thereby produced.

BACKGROUND OF THE INVENTION

The class of thermoplastic polymers is well known in the art, in part because of the useful characteristic of many of such materials of being heat deformable at relatively low temperatures. Such thermoplastics are processed by conventional methods such as extrusion, injection molding or thermoforming into films, sheets, fibers and molded objects of established utility. The physical performance of many if not most thermoplastics suffers, however, when the plastic encounters elevated temperatures or when the plastic is exposed to light, particularly ultra violet light, over an extended period of time. Most thermoplastics undergo some degree of degradation, and in some cases substantial degradation, when maintained under the influence of heat and/or light. As a result, it is frequently if not customarily advantageous to provide protection against the detrimental effects of heat and/or light by incorporating within the thermoplastic one or more stabilizers. Such heat or light stabilizers are particularly necessary in the case of engineering thermoplastics where exposure to elevated temperatures is anticipated either because of the relatively high processing temperatures required or because of a forseen application of the thermoplastic at high temperature.

Many of the conventional stabilizers contain atoms other than carbon and hydrogen and a number of the stabilizers contain heterocyclic rings. Russell et al, U.S. Pat. No. 3,929,729 and U.S. Pat. No. 4,024,104, disclose the use of certain benzophenones and certain benzotriazoles as heat stabilizers in olefin-carbon monoxide polymers. Mercaptobenzothiazoles are a well known class of such stabilizers. It would be of advantage to provide a novel class of heterocyclic heat or light stabilizers for thermoplastic polymers.

SUMMARY OF THE INVENTION

The present invention provides a class of novel heterocyclic compounds as well as a method for producing them. More particularly, the invention relates to the reaction of, and the reaction product therefrom, an o-phenylene compound and a source of a $C_5$ keto-containing moiety, which source is selected from 4-oxoheptanedioic acid compounds or 1,6-dioxa [4.4] spirodilactones.

DESCRIPTION OF THE INVENTION

The novel compounds of the invention comprise two benzoheterocyclic moieties connected by a five-carbon keto-containing connecting group. The source of this five-carbon keto-containing group, i.e., a keto-$C_5$ source, is a 4-oxoheptanedioic acid compound or a 1,6-dioxa [4.4] spirodilactone. The products are 1,5-di(benzoheterocyclic)pentane derivatives having a keto group in the 3-position of the connecting five-carbon group.

In one modification of the process of the invention, the keto-$C_5$ source is a ketodicarboxylic acid compound having two carbon atoms between the keto group and each carboxy function. Expressed in different terms, the keto-$C_5$ source in this modification is a 4-oxoheptanedioic acid compound. Although a variety of such 4-oxoheptanedioic acid compounds having a variety of substituents in addition to the keto group and the carboxy functions are useful, the preferred 4-oxoheptanedioic acid compounds have up to 30 carbon atoms and are represented by the formula

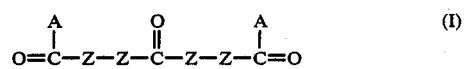

wherein A independently is hydroxy, alkoxy, preferably lower alkoxy of up to 4 carbon atoms inclusive, or halo, preferably the middle halogens chloro or bromo. The term Z independently is $>C(Z')_2$ in which Z' independently is hydrogen, lower alkyl, preferably methyl, halogen, preferably the lower halogens fluoro and chloro, or aryl, preferably phenyl, or Z is such that two adjacent Z moieties taken together form a ring system Z'' of from 5 to 7 ring atoms inclusive, up to two of which are heteroatoms selected from nitrogen, oxygen and sulfur with the remainder of the ring atoms being carbon atoms, there being up to 15 carbon atoms in each Z'', two of which form a bridge between the carbon atoms connected by the adjacent Z moieties. When the Z moieties taken together form a ring system, the ring system is aromatic, cycloaliphatic or heterocyclic and is hydrocarbyl containing only atoms of carbon and hydrogen besides any heteroatoms in the ring system or is substituted hydrocarbyl containing additional atoms such as halogen, preferably lower halogen, in the form of inert carbon atom substituents.

In one embodiment employing the ketodiacid compound spirodilactam precursor, each Z moiety is $>C(Z')_2$ and the ketodiacid compound is an acyclic 4-oxoheptanedioic acid compound. In one such embodiment, largely because of a particularly convenient method of producing the spirodilactam precursor, a preferred 4-oxoheptanedioic acid compound has at least one hydrogen on the carbon atom adjacent to each carboxy function, that is, at least one Z' on each carbon atom adjacent to a carboxy function will be hydrogen. Such 4-oxoheptanedioic acid compounds are represented by the formula

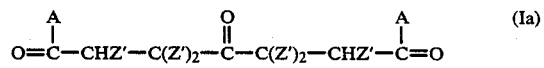

wherein A and Z' have the previously stated meaning. Such 4-oxoheptanedioic acid compounds include 4-oxoheptanedioic acid, dimethyl 4-oxoheptanedioate, 2,6-dimethyl-4-oxoheptanedioic acid, 2,3,5,6-tetramethyl-4-oxoheptanedioyl chloride, di-n-propyl 2,6-di-n-butyl-4-oxoheptanedioate and 6-carbomethoxy-3,3,5,5-tetramethyl-4-oxohexanoic acid. The preferred ketodiacid compounds of the above formula Ia are those wherein each Z' is hydrogen or methyl, especially hydrogen, and each A is hydroxy or methoxy, especially hydroxy.

These ketodicarboxylic compounds are known compounds or are produced by known methods, but certain of the esters of the above formula Ia, i.e., the compounds wherein A is alkoxy, are produced by the reaction of formaldehyde with an α,β-ethylenically unsaturated carboxylic acid ester such as methyl acrylate, ethyl methacrylate, methyl crotonate, methyl ethacrylate and propyl 2,2-dimethylbutanoate. This reaction is conducted in the presence of a catalyst system which comprises a thiazolium salt and a tertiary amine and produces the dialkyl 4-oxoheptanedioate derivative in good yield. This process is described in greater detail in copending U.S. patent application Ser. No. 171,999, filed Mar. 23, 1988, now U.S. Pat. No. 4,800,231, incorporated herein by reference. Conversion of the esters thereby obtained to free acids or acid halides is by conventional methods as is the interconversion of the acids, esters or acid halides of formula Ia in general.

In a second embodiment of the ketodiacid compound spirodilactam precursor, the 4-ketodiacid incorporates cyclic moieties between the keto group and the carboxy function, i.e., two adjacent Z moieties form a cyclic ring structure Z″. Such diacid compounds are represented by the formula

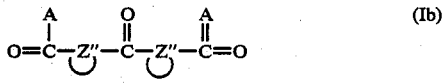
(Ib)

wherein Z″ has the previously stated meaning. Illustrative of these cyclic ketodiacids are di(2-carboxycyclohexyl) ketone, di(2-carboxyphenyl) ketone, di(2-carbopropoxycyclo-4-pentenyl) ketone, di(3-chlorocarbonylphenyl) ketone, di(2-carboxypyridyl) ketone, 2-carboxyphenyl N-methyl-3-carboxy-2pyrryl ketone, di(3-carbethoxy-2-morpholyl) ketone and di(3-carbomethoxy-2-naphthyl) ketone. The preferred cyclic ketodiacid compounds of formula Ib are those wherein each Z″ is a ring system of from 5 to 6 atoms inclusive and up to one nitrogen heteroatom.

The dicyclic 4-ketodicarboxylic acid compounds of formula Ib are known compounds or are produced by known methods, for example, by the method of U.S. Pat. No. 1,999,181 or the method of Cava et al, J. Am. Chem. Soc., 77 6022 (1955), incorporated herein by reference.

In yet another modification of the ketodicarboxylic acid compound as the keto-C₅ source, the ketodicarboxylic acid compound incorporates one cyclic moiety with the remainder of the Z moieties being acyclic, i.e., the compounds represented by the formula

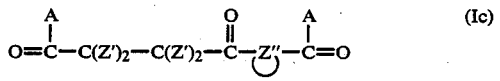
(Ic)

wherein A, Z′ and Z″ have the previously stated meanings. Such ketodiacids of one cyclic moiety are illustrated by 3-(2-carboxybenzoyl)propionic acid, 3-(2-carbomethoxy-2-pyridyloyl)-2-ethylpropionic acid, ethyl 3-(2-carbethoxybenzoyl)propionate and 3-(2-carboxy-4-methylbenzoyl)butyrl chloride. The ketodiacids of the above formula Ic are known compounds or are produced by known methods. For example, 2-carboxymethylbenzaldehyde reacts with methyl acrylate according to the general teachings of copending U.S. patent application Ser. No. 171,999, filed Mar. 23, 1988 now U.S. Pat. No. 4,800,231.

In a second embodiment of the invention, the keto-C₅ source is a 1,6-dioxospiro[4.4]nonane-2,7-dione compound in which the spiro ring system is substituted with hydrogen, alkyl or halo groups or which incorporates fused cyclic substituents which include the 3- and 4-spiro ring positions and on the 8- and 9- spiro ring positions of the spirodilactone ring system. One class of such [4.4] spirodilactones is represented by the formula

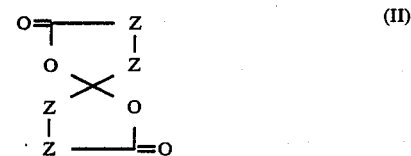
(II)

wherein Z has the previously stated meaning.

In the modification of these spirodilactone compounds as the keto-C₅ source wherein each Z is >C(Z′)₂, the spirodilactam compounds are represented by the formula

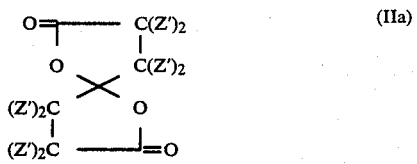
(IIa)

wherein Z′ has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]nonane-2,7-dione, 4,9-diethyl-1,6-diazaspiro[4.4]nonane-2,7-dione, 3,3,8,8tetramethyl-1,6-dioxaspiro[4.4]nonane-2,7-dione, 3,3,4,4,8,8,9,9-octamethyl-1,6-dioxaspiro[4.4]nonane-2,7-dione and 3,4,8,9-tetrafluoro-1,6-dioxaspiro[4.4]nonane-2,7-dione. The preferred spirodilactones of the above formula IIa are those wherein at least one Z′ of each Z′-substituted carbon atom is hydrogen.

The compounds of formula IIa are known compounds or are produced by known methods such as the process of Pariza et al, Synthetic Communications, Vol. 13 (3), pp. 243–254 (1983).

In the modification of the spirodilactone compounds as the keto-C₅ source in which a cyclic moiety is a substituent on each of the two rings of the spiro ring system, the spirodilactone compounds are represented by the formula

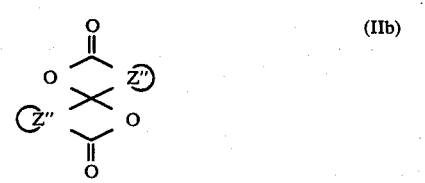
(IIb)

wherein "Z" has the previously stated meaning. Typical compounds of this formula IIb are 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di(4-methylbenzo)-1,6-dioxaspiro[4.4]nonane-2,7-dione and 3,4,8,9-di-(pyrido)-1,6-dioxaspiro[4.4]nonane-2,7-dione. These compounds are known compounds or are produced by known methods, for example, the process of the above Cava et al article or by the process of U.S. Pat. No. 1,999,181.

In a third modification of the spirodilactone compounds as the keto-C₅ source, a cyclic moiety is fused to one spiro ring as a substituent and the other spiro ring is free from fused cyclic substituents. These spirodilactone compounds are represented by the formula

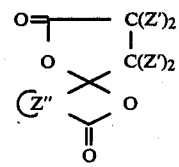
(IIc)

wherein Z' and Z" have the previously stated meanings. Such spirodilactones are illustrated by 3-methyl-8,9-benzo-1,6-dioxaspiro[4.4]nonane-2,7-dione, 3,4-benzo-1,6-dioxaspiro[4.4]nonane-2,7-dione, and 3,3,4,4-tetramethyl-8,9-morphols-1,6-diazaspiro[4.4]nonane-2,7-dione. The spirodilactones of the above formula IIc are produced by known methods, for example, the dehydration of the corresponding ketodiacid. By way of illustration, 3,4-benzo-1,6-dioxaspiro[4.4]nonane-2,7-dione is produced by dehydration of 3-(2-carboxybenzoyl)propionic acid through application of heat.

In general, the preferred spirodilactone compounds to be used as a keto-C₅ source are hydrocarbon except for the oxygen atoms of the lactone moieties, particularly those spirodilactone compounds which are free from fused ring substituents (formula IIa) or those which have a fused ring substituent on each of the spiro rings (formula IIb). An especially preferred spirodilactone spirodilactam precursor of the first class is 1,6-dioxaspiro[4.4]nonane-2,7-dione while a preferred spirodilactone of the latter class is 3,4,8,9-dibenzo-1,6-dioxaspiro[4.4]nonane-2,7-dione.

The keto-C₅ source, whether a ketodicarboxylic acid compound or a spirodilactam compound, is reacted in the process of the invention with an ortho-phenylene amine compound. These amine compound reactants are organic compounds having an aromatic ring which is substituted on adjacent carbon atoms with a first substituent which is an amino substituent, i.e., a -NH₂ group, and a second substituent which is amino, alkylamino, hydroxy or thiol. The ortho substitution is required for the process of the invention since substitution of the amino group and the second substituent in any relationship other than ortho precludes the formation of the desired heterocyclic products. The formation of such products also requires the presence of the two hydrogen substituents on the amino group and at least one hydrogen on any nitrogen-containing second substituent. One class of such o-phenylene amine compounds is represented by the formula

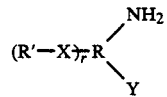
(III)

wherein R is aromatic of up to 20 carbon atoms and from 1 to 2 aromatic rings, inclusive, R' is R or aliphatic of up to 10 carbon atoms inclusive, r is 0 or 1, Y is amino, alkylamino, hydroxy or thiol and X is a direct valence bond, alkylene of up to 8 carbon atoms inclusive, oxy, thio, sulfonyl, carbonyl, dioxyphenylene, i.e.,

2,2-di(oxyphenyl)propane, i.e.,

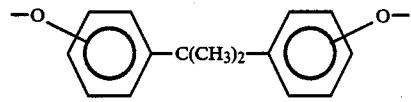

di(oxyphenyl)sulfone, i.e.,

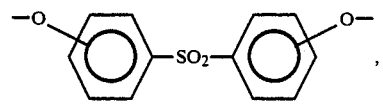

or dioxydiphenylene, i.e.,

with the proviso that the -NH₂ and the Y are substituted on adjacent carbon atoms. R, R' and X are otherwise hydrocarbyl containing only atoms of carbon and hydrogen besides any additional atoms present as divalent linking groups or is substituted hydrocarbyl containing additional atoms such as halogen, preferably middle halogen, present as inert carbon atom substituents.

Illustrative of the o-phenylene amine compound reactants of the above formula III are o-phenylenediamine, 3,4-toluenediamine, 1,2-diaminonaphthalene, 4,5-dichloro-1,2-diaminobenzene, 3,4-diaminobiphenyl, 1,2-diamino-4-phenoxybenzene, 1,2-diamino-4-benzoylbenzene, 2,3-diamino-5-phenylsulfonylnaphthalene, 1-amino-2-methylamino-4-phenylthiobenzene, 1-ethylamino-2-amino-3-(4-phenoxyphenyl)benzene, 1-ethylamino-2-amino-3-(4-phenoxyphenyl)benzene, o-aminophenyl, 6-chloro-2-aminophenol, 4-(3-bromophenyl)-2-aminophenol, 2-amino-3-hydroxynaphthylene, o-aminothiophenol, 4-methyl-2-aminothiophenol,5-chloro-2-mercapto-3-aminonaphthalene and 2-amino-3-mercapto-4'-methylbiphenyl. In general, the preferred o-phenylene amine compounds are those wherein the compound is otherwise hydrocarbyl, especially those o-phenylene amine compounds wherein r is 0. Also preferred are the phenylene diamines over the corresponding alkylaminoamines, aminophenols or aminothiophenols. Ortho-phenylenediamine is particularly satisfactory.

The reaction of the keto-C₅ source and the o-phenylene amine compound is conducted in a liquid phase in the presence of an inert reaction diluent. Suitable reaction diluents are liquid at reaction conditions and are polar diluents in which the keto-C₅ source and the o-phenylene amine compound are at least partially soluble at reaction temperature. Such diluents include ketones such as methylisobutyl ketone and di-n-propyl ketone, esters such as ethyl 2-ethylhexanoate, ethers including acyclic esthers such as diethylene glycol diethyl ether and tetraethylene glycol dimethyl ether as well as cyclic ethers such as dioxane and tetrahydrofuran, N-alkylamides such as N,N-dimethylformamide, N,N-dimethylacetamide and N-methyl-2-pyrrolidone, phenols such as phenol and m-cresol and sulfur-containing diluents such as dimethyl sulfoxide and sulfolane. The preferred reaction diluent is m-cresol.

The keto-$C_5$ source and the o-phenylene amine compound combine in a 1:2 molar ratio to produce the heterocyclic derivatives of the invention. Although it is satisfactory to provide the keto-$C_5$ source and the o-phenylene amine compound to the reaction mixture in molar ratios of from about 2:1 to about 1:8 and even higher or lower reaction ratios may be utilized, molar ratios from about 1:1 to about 1:4 are preferred. Reactant contact is maintained during reaction by conventional techniques such as shaking, stirring or refluxing. Suitable reaction temperatures are from about 125° C. to about 275° C., preferably from about 150° C. to about 250° C., depending in part upon the particular reaction diluent to be employed. The reaction pressure will be sufficient to maintain the reaction mixture in the liquid phase. Typical reaction pressures are up to about 20 atmospheres, more typically from about 0.8 atmosphere to about 10 atmospheres.

Reaction of the keto-$C_5$ source and the o-phenylene amine compound results in the formation of a benzoheterocyclic which incorporates one carbon atom of the keto-$C_5$ source in each of two heterocyclic ring systems, which rings are thus connected by the resulting five-carbon bridge which is derived from the keto-$C_5$ source and has a keto function in the center or 3-position. The derivative will be a benzoimidazoyl derivative, a benzoxazoyl derivative or a benzothiazoyl derivative if the o-phenylene amine compound is a diamine, an aminophenol or an aminothiophenol, respectively. In terms of the keto-$C_5$ source of either formula I or formula II and the o-phenylene amine compound of formula III, the heterocyclic products are represented by the formula.

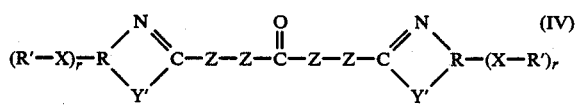

(IV)

wherein R, R', r and Z have the previously stated meanings, and Y' is the moiety derived by loss of a hydrogen from Y, i.e., imino, alkylimino, oxy or thio, with the proviso that the indicated nitrogen and Y' are substituted on adjacent carbon atoms of R. In terms of the preferred reactants of formulas I or II and III, the preferred products of formula IV are those wherein each r is 0 and Z is $>CH_2$ or adjacent Z groups are benzo.

Illustrative of such products are 1,5-di(2-benzimidazoyl)-3-oxopentane, produced from o-phenylenediamine and 4-oxoheptanedioic acid or 1,6-dioxaspiro[4.4]nonane-2,7-dione 1,5-di(N-methyl-2-benzimidazoyl)-1,2,4,5-dibenzo-3-oxopentane produced from 2-ethylaminoaniline and di(2-carboxyphenyl) ketone or 3,4,8,9-dibenzo-1,6-dioxaspiro[4.4]nonane-2,7-dione, 1,5-di(5-methyl-2-benzothiazoyl)-1,5-dimethyl-3-oxopentane produced from 2-amino-6-methylthiophenol and 2,6-dimethyl-4-oxoheptanedioic acid or 3,8-dimethyl-1,6-dioxaspiro[4.4]nonane-2,7-dione, and 1,5-di(4-chloro-2-benzoxazoyl)-3-oxopentane produced from 4-chloro-2-aminophenol and 4-oxoheptanedioic acid or 1,6-dioxaspiro[4.4]nonane-2,7-dione. Other products will be apparent from consideration of the above formulas for the reactants and the heterocyclic products.

The heterocyclic derivatives of the invention are stabilizers, particularly thermal stabilizers, for a variety of thermoplastic polymers and particularly engineering thermoplastics such as polyvinyl chloride, the polycarbonates and the polysulfones. They are employed in the amounts conventionally utilized for such stabilizers, generally a few percent by weight or less, based on stabilized composition. The thermoplastic polymer is stabilized through the formation of an intimate mixture of the polymer to be stabilized and the heterocyclic stabilizer, which mixture is produced by conventional methods of mixing or blending of the polymer and stabilizer.

The invention is further illustrated by the following Illustrative Embodiment which should not be construed as limiting the invention.

ILLUSTRATIVE EMBODIMENT

A mixture of 17.4 g (0.1 mole) of 4-oxoheptanedioic acid, 21.6 g (0.2 mole) of o-phenylenediamine and 100 ml of m-cresol was placed in a 500 ml resin pot equipped with a mechanical stirrer and a condenser. The mixture, while being stirred, was warmed to 200° C. and maintained at that temperature for 12 hours. The resulting mixture was then cooled and poured into 500 ml of methylene chloride. The precipitated product was recovered by filtration, washed several times with methylene chloride and dried in a vacuum oven at 150° C. for 24 hours. The melting point of the product was 210° C. and the nuclear magnetic resonance spectra were consistent with the structure 1,5-bis(2-benzimidazoyl)-4-oxopentane.

What is claimed is:

1. The 1,5-di(benzoheterocyclic)-3-oxopentane compound of the formula

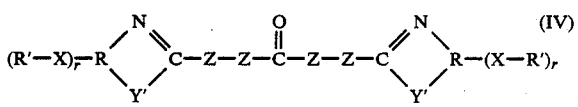

(IV)

wherein R is aromatic of up to 30 carbon atoms and from 1 to 2 aromatic rings, inclusive, R' is R or aliphatic of up to 10 carbon atoms inclusive, r independently is 0 or 1, Y' is imino, alkylimino, oxy or thio, X is a direct valence bond, alkylene of up to 8 carbon atoms inclusive, oxy, thio, sulfonyl, carbonyl, dioxyphenylene, 2,2-dioxyphenyl)propane, di(oxyphenyl) sulfone or dioxydiphenylene and Z independently is $>C(Z')_2$ in which Z' independently is hydrogen, lower alkyl, lower halogen or phenyl, or Z is such that adjacent Z moieties form a ring system Z" of from 5 to 7 ring atoms, up to two of which are heteroatoms selected from nitrogen, oxygen or sulfur with the remainder of the ring atoms being carbon atoms, there being up to 15 carbon atoms in each Z", two of which form a bridge between the carbon atoms connected by the adjacent Z moieties, with the proviso that N and Y' are substituted on adjacent carbon atoms of R.

2. The compound of claim 1 wherein r is 0.

3. The compound of claim 2 wherein Z is $>C(Z')_2$.

4. The compound of claim 3 wherein Z' is hydrogen or methyl.
5. The compound of claim 4 wherein Y' is imino.
6. The compound of claim 4 wherein R is phenylene.
7. The compound of claim 6 wherein Z' is hydrogen.
8. The compound of claim 4 wherein Y is oxy.
9. The compound of claim 4 wherein Y' is thio.
10. The compound of claim 2 wherein adjacent Z moieties are Z''.
11. The compound of claim 10 wherein Y' is imino.
12. The compound of claim 11 wherein R is phenylene.

* * * * *